United States Patent [19]

Marks

[11] Patent Number: 5,168,901
[45] Date of Patent: Dec. 8, 1992

[54] FLUID COMMUNICATION MANIFOLD AND CONTROL SYSTEM

[76] Inventor: Lloyd A. Marks, 727 Great Springs Rd., Bryn Mawr, Pa. 19010

[21] Appl. No.: 705,059

[22] Filed: May 23, 1991

[51] Int. Cl.[5] ............................................. F16K 5/08
[52] U.S. Cl. ..................................... 137/884; 251/289
[58] Field of Search ........................ 251/292; 137/884; 251/289

[56] References Cited

U.S. PATENT DOCUMENTS

| | | | |
|---|---|---|---|
| 3,664,372 | 5/1972 | Marshall | 251/292 X |
| 4,131,133 | 12/1978 | Huwe | 251/292 X |
| 4,232,709 | 11/1980 | Zoric | 251/289 X |
| 4,637,423 | 1/1987 | Gray | 251/292 X |
| 4,819,653 | 4/1989 | Marks | 251/129.05 X |
| 4,887,634 | 12/1989 | Killian | 251/292 X |

FOREIGN PATENT DOCUMENTS

1468803  3/1977  United Kingdom ................ 251/289

*Primary Examiner*—John C. Fox
*Attorney, Agent, or Firm*—Wigman & Cohen

[57] ABSTRACT

A multi-function fluid communication control system for effecting selective automated control of fluid communication between fluid sources and instruments is disclosed. The system comprises a disposable stopcock manifold having a plurality of stopcocks adapted to be releasably connected to an actuator system which automatically operates the stopcocks. The stopcocks may also be manually operated to override the automatic operation of the stopcocks. The actuator system for the stopcock manifold is controllable by a microprocessor.

16 Claims, 6 Drawing Sheets

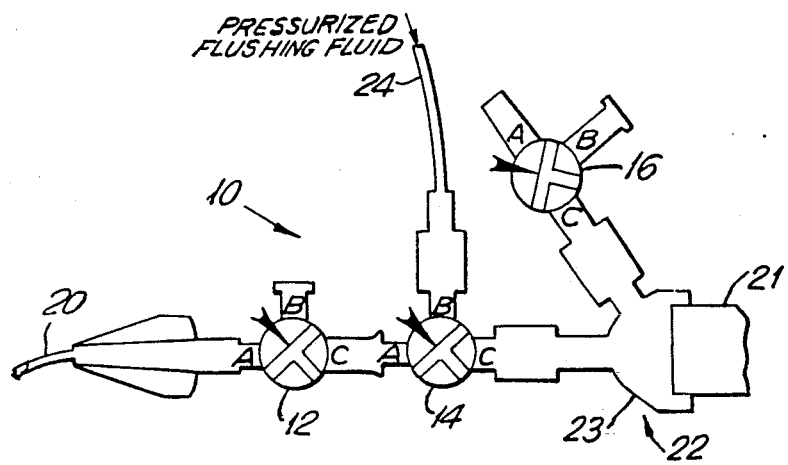
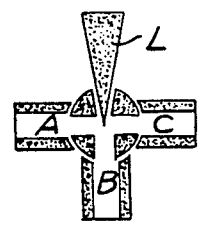
FIG.1                    FIG.1a
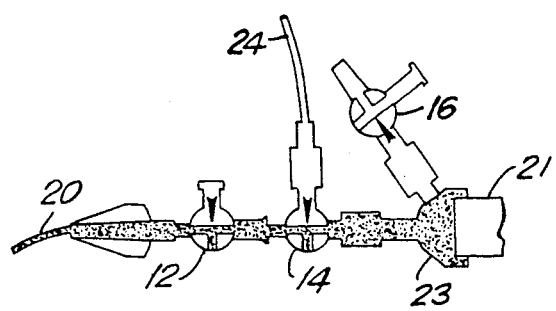
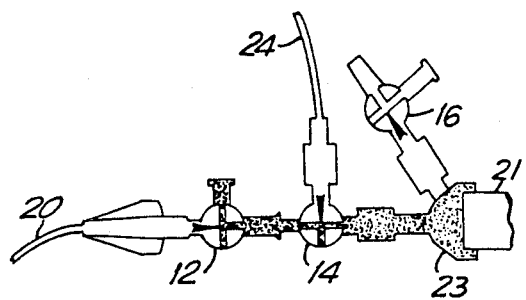
FIG.2                    FIG.4
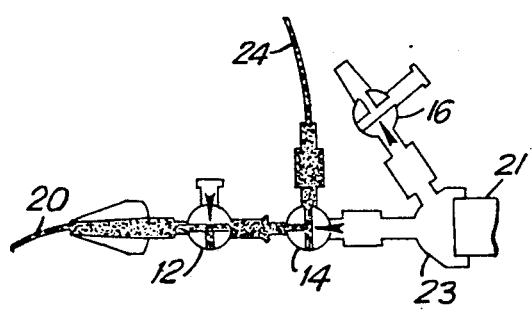
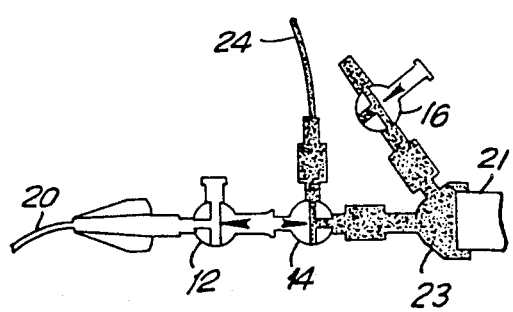
FIG.3.                   FIG.5

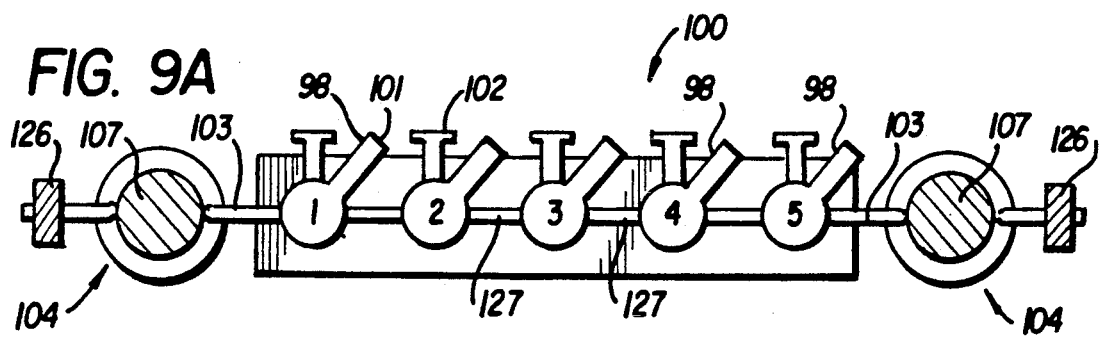
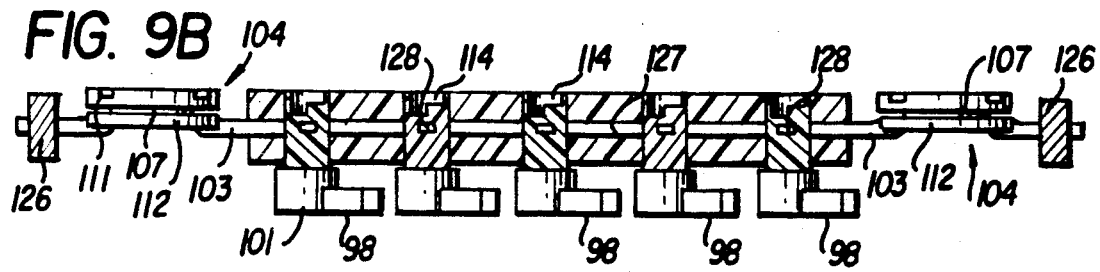
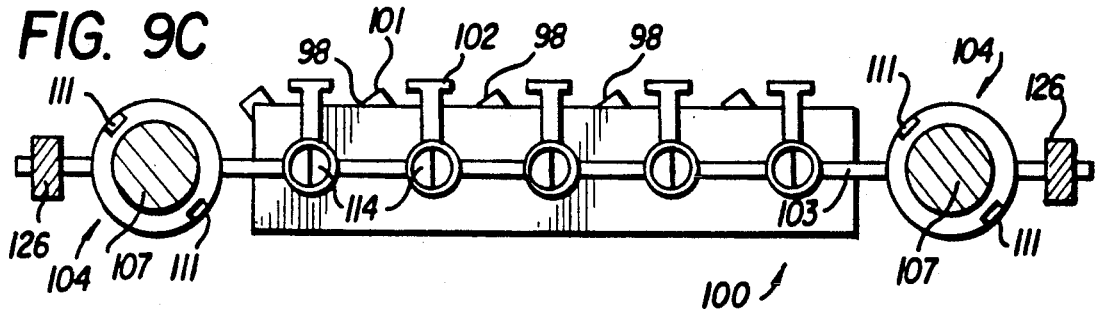
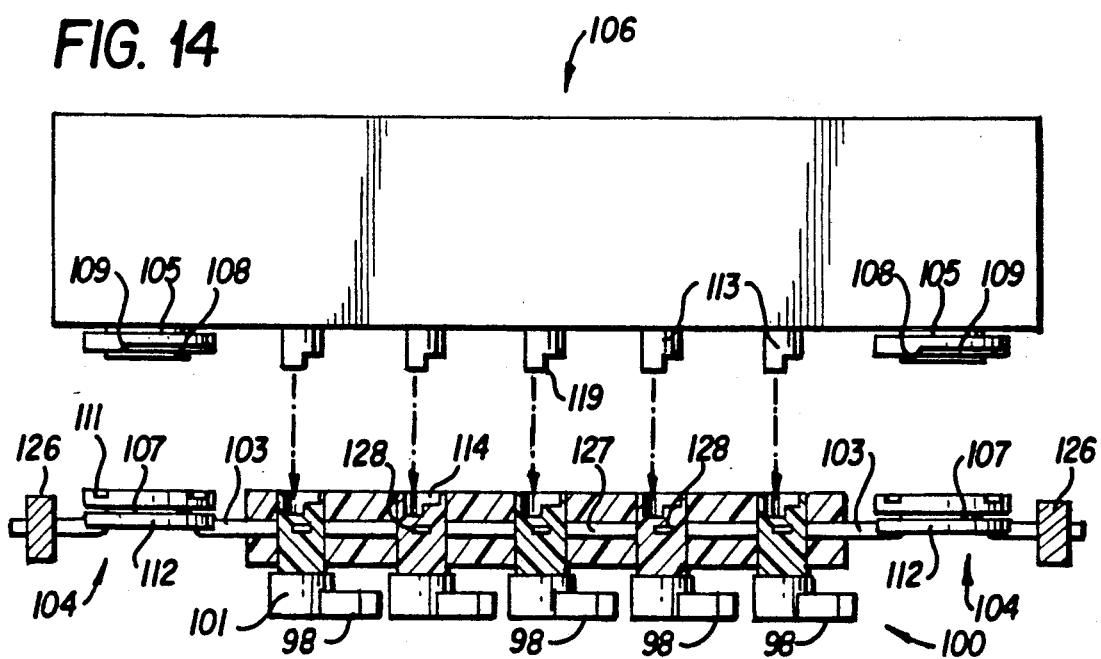

FLUID COMMUNICATION MANIFOLD AND CONTROL SYSTEM

FIELD OF THE INVENTION

The present invention relates to the art of controlling fluid communication between and among various fluid ports to effect hydraulic communication between fluid reservoirs, sources, instruments, as well as various pressure conditions, and more particularly to a disposable manifold for use with a fluid control system.

BACKGROUND OF THE INVENTION

It has been known in the art of multiple hydraulic connection to provide series of multiple port valves in order to effect desired fluid communication paths for many purposes. For example, since it is generally required to provide various fluid communication paths in order to measure pressure, calibrate equipment and clean and purge hydraulic systems, multi-port valves can be used which combine fluid connection and blockage of multiple hydraulic communication ports. In the case of medical applications, hydraulic connections can be particularly critical especially since hydraulic lines can be in direct communication with human fluid conduits such as vessels, arteries, etc. Thus, a failure of a hydraulic system could result in severe damage to the patient.

Furthermore, in the art of medical care it has been known to provide a computer controlled medical care system in which automatic or manual control of a variety of medical procedures including diagnostic procedures can be carried out. Thus, in U.S. Pat. No. 4,464,172 to Lichtenstein, it is known to perform a number of procedures such as infusion of physiologic fluids, monitoring of hemodialysis, ultrafiltration, hemofiltration, medical drainage and irrigation procedures, etc. This system is designed basically to monitor, by use of sensors, the flow to or from the body and to generate command signals necessary to either stop, start, or otherwise modify the flow into or out of the body and/or effect analysis of such fluid.

In U.S. Pat. No. 4,112,272 to Jonsson et al. a measuring device is disclosed which transmits signals to a device having an electro-mechanical switch and valve mechanism for switching off to automatic zero balance and automatically calibrate. This disclosure shows the manipulation of an instrument responsive to flow in and out of a body wherein a signal is generated to a control unit.

While these devices, as well as others, may prove adequate with regard to flow directly into and out of a body, they are inadequate for operation of a multifunction fluid communication system which requires simultaneous and/or step-wise control of multi-port control valves connecting various fluid sources, reservoirs, instruments, and fluid-effecting environments.

There has been, however, a need for a multifunction fluid communication control system in the medical field, especially in an area of catheterization processes and systems. In a cardiac catheterization procedure, a flexible plastic tube is positioned in the heart to perform various diagnostic tests, and several fluid communication paths must be continuously established in order to perform the many tasks associated with making a proper diagnosis. For example, not only do the doctor and attending technicians have to be able to continuously monitor pressure within the cardiac chambers, but the system must continuously or periodically be flushed to remove blockages and clotting, as well as periodic calibration be performed on the pressure measuring instrumentation in order to achieve accurate readings.

Other procedures not associated with catheterization also require a multi-function fluid communication control system to combine operations such as infusion, flushing, pressure measurement, dye injection, blood extraction, etc., which require simultaneous and step-wise control of various fluid and pressure conditions.

In my U.S. Pat. No. 4,819,653, the subject matter of which is incorporated herein by reference, there is disclosed a multi-function, fluid communication control system for simultaneous and stepwise connection of fluid communication between ports of hydraulically connected multi-port fluid communication valves. That control system solved many of the drawbacks associated with the prior art devices.

SUMMARY OF THE INVENTION

The present invention relates to certain improvements in my prior invention including a disposable stopcock manifold and pressure dome structure and an actuator system which provides for remote control or manual operation of the stopcocks of the manifold.

The disposable stopcock manifold is coupled from behind to a stopcock actuator so that manual operation of the stopcocks is still possible from the front by means of the usual stopcock handle mechanism. The actuator includes motors and gearing for automatically positioning the stopcocks in response to a programmed control signal and a feedback system for providing a signal when the stopcocks are properly positioned.

In the illustrated embodiment, the disposable manifold includes pressure domes which may be mechanically coupled by membranes to pressure transducers located in the actuator for measuring manifold pressure. Alternatively, disposable pressure transducers could be included with the disposable manifold.

According to the present invention, the preferred embodiment incorporates the following features:

1. The manifold is coupled from behind, thereby providing a normal stopcock configuration when viewed from the front which can be used optionally at the discretion of the medical personnel.
2. The ability to increase torque by using a gearing system.
3. Integration of a pressure measuring means into the disposable manifold configuration.
4. One or more remote controllers which may be of a wireless type.
5. Programmability, i.e., customization of response to a given pushbutton on a controller according to user preference.
6. Alternate use of a motor which is not of a stepper type.
7. Addition of an in-line bubble detector.
8. Optional configurations of system functions such as providing an advance warning tone before automatic flushes or eliminating automatic flushes in favor of a reminder tone which prompts the physician to manually flush the catheters.

For a better understanding of the present invention, together with other and further features, reference is made to the following description, taken in conjunction with the accompanying drawings and in the appended claims.

BRIEF DESCRIPTION OF THE DRAWINGS

A preferred embodiment of the invention has been chosen for purposes of illustration and description and is shown in the accompanying drawings. For a better overall understanding of the present invention a description of my prior invention is also included.

FIG. 1 is a schematic of a system in accordance with my prior invention which can be used in a cardiac catheterization process;

FIG. 1a is a schematic of a three-way stopcock which can be used in my prior invention;

FIGS. 2-5 are schematic views which show the different settings required for effecting the different modes of operation in, for example, a catheterization process;

FIG. 6a is a view of the mechanical linkage in FIG. 6 taken from lines 6a-6a;

FIGS. 9A-9C are front, cross-section and rear views, respectively, of a disposable stopcock manifold and pressure dome structure of the present invention;

FIG. 14 is a composite of FIGS. 9B and 10B, illustrating the mating of the actuator with the manifold as viewed from above.

DETAILED DESCRIPTION OF THE INVENTION

Referring to FIGS. 1-8, there can be seen a multifunction, fluid communication control system which can be used to make simultaneous or step-wise hydraulic connections between various sources and reservoirs of fluid as well as different instrumentation and pressure conditions. In particular, the system shown in the FIGS. depicts one which is particularly useful in a cardiac catheterization process.

A cardiac catheterization process provides a means to probe the heart region and detect any diseases or malfunctions. One of the major problems in the procedure is the inefficiency which occurs when technicians have to take time to turn the various multi-port valves or stopcocks in order to achieve the different process conditions.

As a part of the process, a catheter, which is a thin, flexible plastic tube, is passed through a blood vessel and into the heart for measuring pressures, taking blood specimens, and administering medications or radi-opaque dyes for cineangiography (high speed motion X-rays). In order to perform these tasks, connections must be made in varying combinations between the cardiac catheter, a pressure transducer, a pressurized flush solution, and ambient atmosphere. In FIG. 1 a schematic is shown in the system 10 which is used in such a process. In particular, there are shown three stopcocks, 12, 14, and 16, each one of which has three fluid communication ports A, B and C.

Figure 6:
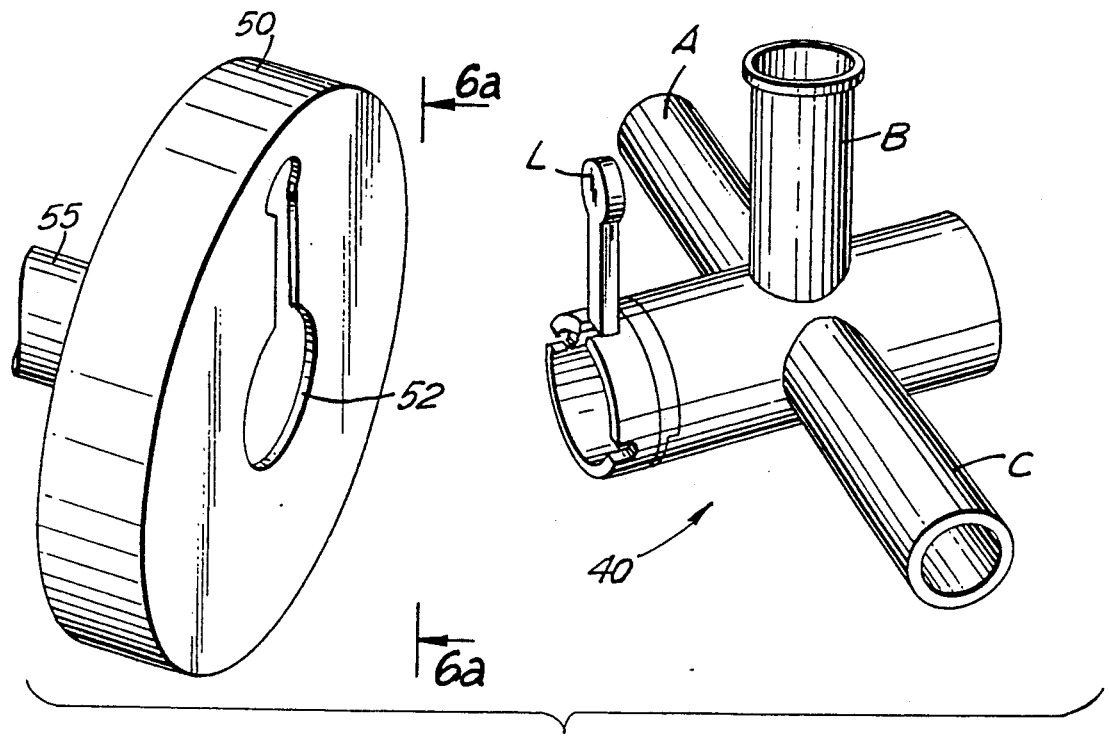
FIG. 6 is an exploded perspective view of a typical stopcock used in the process shown in FIGS. 1-5 and a mechanical linkage which can be attached thereto.

With particular reference to FIG. 1A, it can be seen that the stopcocks which are useful in the system shown herein have an internal rotating T-shaped channel which establishes connections for fluid communication among the three ports. FIG. 6 illustrates a perspective view of a typical stopcock used in a catheterization procedure. The stopcocks are arranged so that when the lever L points towards one of the three channels, that channel is disconnected from the other two, the other two having fluid communication established therebetween. Thus, when the lever is pointed toward the B port, the B port is closed to fluid communication while ports A and C are hydraulically connected. Similarly, when the stopcock lever L is pointed toward the A port, that port is blocked from fluid communication while ports B and C are hydraulically connected; and when the lever L is pointed toward the C port, it is blocked from fluid communication, while ports A and B are hydraulically connected.

In the schematic shown in FIG. 1, a catheter tube 20, which can be passed through a blood vessel and into the heart in a catheterization process is connected for fluid communication to port A of stopcock 12. Port B of stopcock 12 is connected to ambient atmosphere and port C is connected to stopcock 14. Meanwhile, stopcock 14 is connected by its port A to stopcock 12, by port C to a pressure measurement means 22, and by its port B to a source of pressurized flushing fluid.

The pressure measurement means 22 can include a pressure transducer 21 and a pressure measurement dome 23. The pressure transducer dome 23 is usually a clear plastic structure which contains fluid and is used for connection to the catheter. If a dome is used, it must be opened to ambient atmosphere (or room air) in order to calibrate the transducer and recorder.

Stopcock 14 is connected for hydraulic communication with a source of pressurized flushing fluid by line 24, which, in the case of a cardiac catheterization process, can be heparinized saline solution under about 150 mm Hg.

A third stopcock 16 is connected for fluid communication by its outlet port C to the pressure measurement means 22 through dome 23, while ports A and B are opened to the ambient atmosphere.

The principal tasks which require manipulation of the stopcocks during a procedure such as a cardiac catheterization include, in addition to the normal pressure measurement operation, flushing of the catheters, flushing of the pressure dome, and recording of pressure tracings. Since any number of catheters may be used depending on the nature and the purpose of the cardiac catheterization, e.g., in a typical right and left study, two catheters are used, one positioned in an artery and the other in a vein, it is necessary to flush all the catheters every few minutes with a heparinized saline solution to prevent clots from forming. Thus, it can be seen that in order to keep the catheter lines open, a great deal of manipulation is required. Catheters are also flushed every time specimens are withdrawn from them, prior to pressure recordings, and whenever pressure wave forms become damped.

Most of the time during the procedure, the elements of a cardiac catherization system are connected for pressure measurement. As shown in FIG. 2, the stopcocks are positioned to hydraulically connect the catheter directly to the transducer dome 23 (the dark portion represents fluid communication and the arrow shows the position of the stopcock lever). When the system is connected to an automatic function control system, the stopcocks can be left in this position as a default condition.

In FIG. 3, the next mode of operation depicted is a flushing mode, by which the pressurized flushing solution is connected to the catheter. After a flush is completed, the stopcocks can be repositioned to measure pressure. In FIG. 3 the dark portion shows a fluid communication between the source of pressurized flush fluid through line 24 stopcocks 14 adn 12, and hence into the catheter 20.

FIG. 4 shows a configuration used to establish a zero base line with regard to the ambient atmosphere in to make an accurate recording or tracing of the pressure. In particular, FIG. 4 shows fluid communication between the ambient air through stopcock 12 and stopcock 14 and thence to the pressure measurement device 22. After the recorder base line has been calibrated to zero with the stopcocks in this condition, the catheter can be flushed as shown in FIG. 3 and the stopcocks returned to the pressure measurement mode of FIG. 1 so that the pressure can be measured and recorded.

Yet a further operation which must be performed in order to make the system effective for purposes of cardiac catherization is to purge the system of air bubbles which may accumulate in the pressure dome 23 so that pressure readings will not be damped. Consequently, the dome should be flushed clear at least at the beginning of each procedure to purge the air bubbles accumulated therein. In FIG. 5, the stopcocks are shown to establish a fluid communication directly between the source of pressurized flush fluid, the pressure dome, and thence the ambient atmosphere through stopcock 16 for forcing out air bubbles which may be accumulated therein. Inasmuch as bubbles may adhere to the surface of the pressure measurement device and/or the interior surface of the pressure dome, agitation may be needed to jolt the bubbles free from their lodged condition.

In summary, Table 1 shows the correlative positions of each of the stopcock levers for the functions described above.

TABLE 1

| Function | Stopcock #12 | Stopcock #14 | Stopcock #16 |
|---|---|---|---|
| Pressure Measurement | B | B | C |
| Flushing Catheter | B | C | C |
| Transducer Calibration | A | B | C |
| Purging Transducer Dome | B | A | A or B |

Needless to say, manipulating the stopcocks in the catheterization lab is tedious, repetitive an time consuming. The pressure transducer and stopcocks are usually located at some distance apart, so that every time a catheter or pressure dome is flushed, a technician must interrupt his ongoing tasks and walk to and from the stopcocks in order to make the necessary changes in the hydraulic connections. Furthermore, when a pressure recording is made, it is necessary to make at least two trips in order to open the transducer to ambient atmosphere for calibration of the recorder, followed by calibrating the recorder and back again to flush the lines and set them for pressure measurement. In order to eliminate in whole or in part these unnecessary steps, the technician and/or doctor can be provided with a central, even multiple remote controls at more than one station, so that stopcock manipulation can be achieved therefrom without physical movement.

In order to make this process more efficient, it has been found that a mechanical linkage such as that shown on the left hand side of FIG. 6 can be provided for stopcocks known in the art, which will turn them in response to an instruction signal generated by an appropriate control unit 60. Thus, the system can take user input via even remote control switches and effect mechanical turning of the stopcocks simultaneously or step-wise thus saving time and allowing operators to accomplish more by doing other required procedural tasks.

In particular, there is shown in FIG. 6 a stopcock 40 having ports A, B and C an a lever L which can fit into a disk 50 mounted on a drive 55. The disk 50, in turn, contains a template depression 52 in the form of lever L and slightly larger than lever L so that the lever can be inserted into the depression for being driven simultaneously therewith. The drive shaft 55 in turn can be connected to stepper motors 70 which can be rotated in precise increments in a clockwise or counterclockwise direction. While the invention is not intended to be so limited, it has been found that this is a particularly useful mechanical linkage for the present process since it can be made to be compatible with known equipment techniques.

Figure 6A:
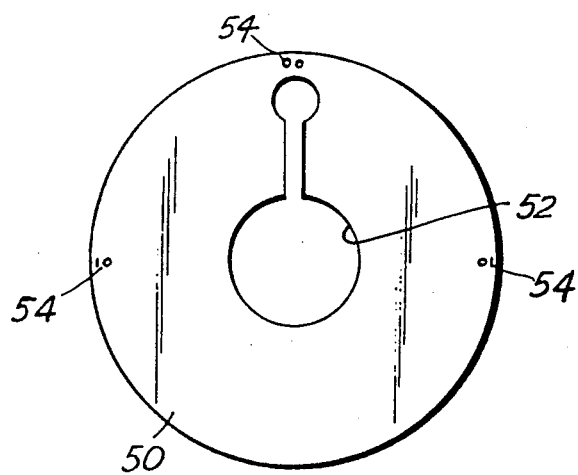

Moreover, the stopcock positions can be easily verified with an optical electronic feedback system by detection of reflective tape 54 shown in FIG. 6A, each position of which can be identified by a two digit binary code. Basically, light reflects from the tape and switches a pair of phototransistors, providing a two-bit digital feedback signal for each stepper motor. Alternatively, other known feedback systems can be employed.

In order to provide the function control to the stepper motor, the system can be provided with a computer control means 60 to send the appropriate electrical signals to each of the stepper motors to effect the different operations. The computer control system can be a combination of a central processing unit and software and drive circuitry, or, in the alternative, can include a microprocessor having appropriately programmed microchips which can effect the different conditions.

Figure 7:
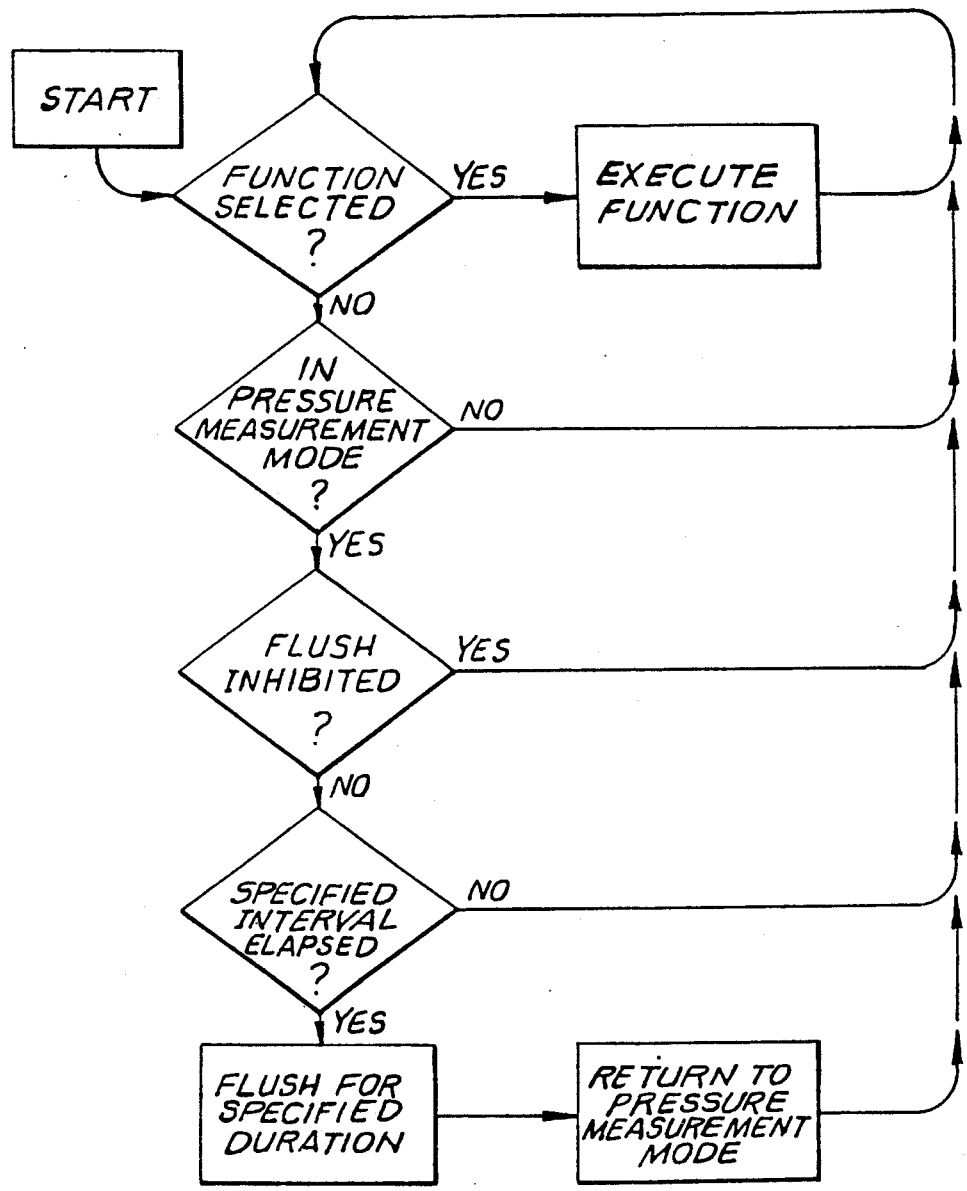
FIG. 7 is an operational flow diagram useful in a computer control means which can be used in my prior invention as well as in the present invention.
Figure 13:
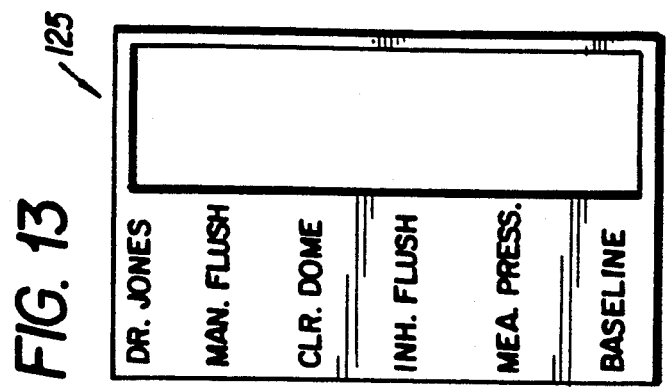
FIG. 13 is a front view of a template which can be positioned over a control panel such as that shown in FIG. 12 to assign customized functions to the pushbuttons of the control unit.
Figure 12:
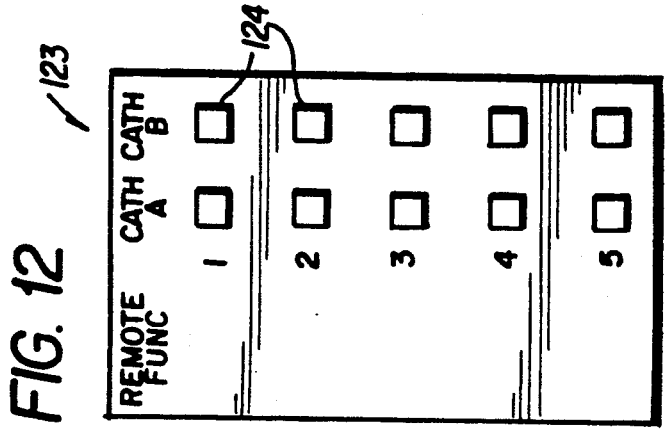
FIG. 12 is a front view of a remote control unit which can be used to perform system functions at a distance.
Figure 8:
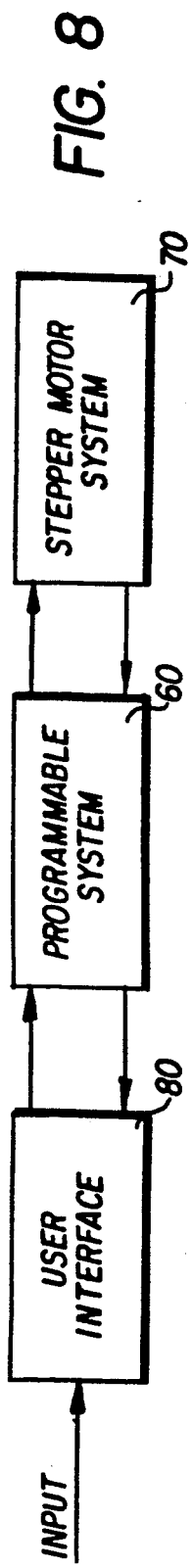
FIG. 8 is a diagrammatical representation of the control system of my prior invention as well as the present invention.
Figure 11:
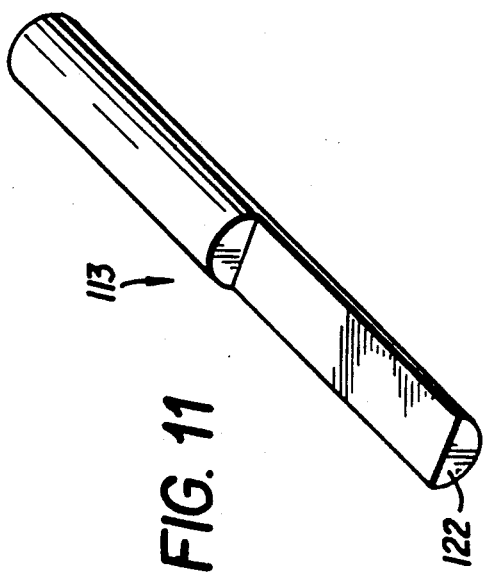
FIG. 11 is a perspective view of a shaft construction which can be used as a mechanical linkage between the electro-mechanical actuator and the disposable manifold system.
Figure 10A:
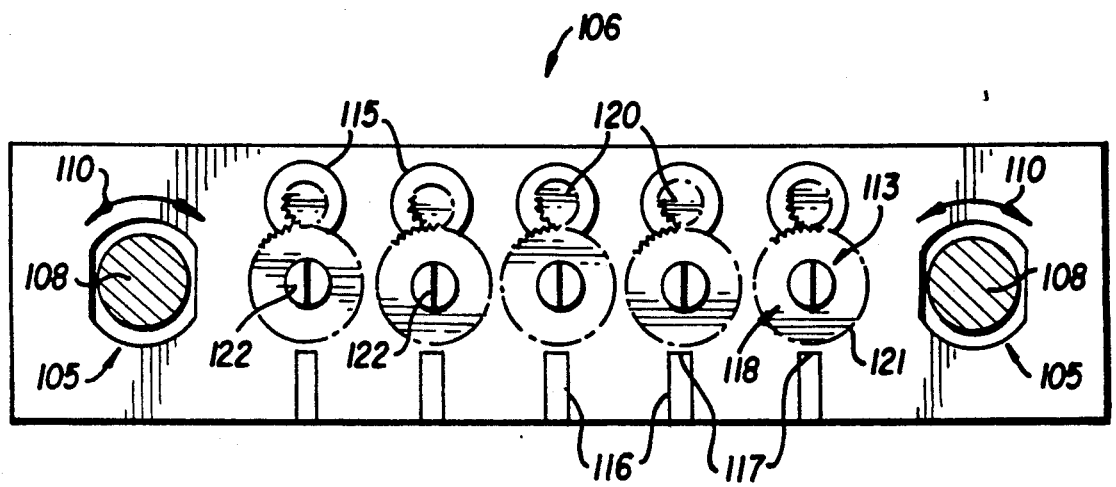
FIGS. 10A and 10B are front and top views of the electro-mechanical actuator system which controls the stopcock position via a series of mechanical linkages.
Figure 10B:
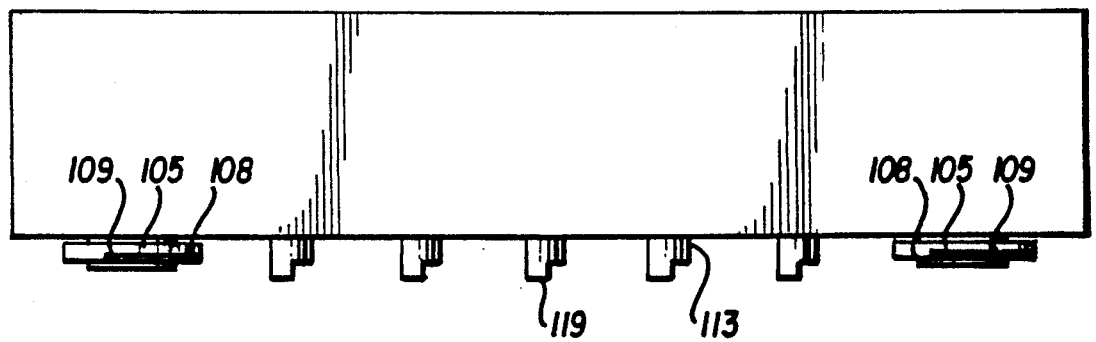

Referring to FIG. 7, a general flow diagram is shown which depicts an effective mode of operation for a computer control used in the present invention. Basically, the computer control continuously interrogates the input 80 from the user to determine if a function has been selected which is outside of the routine operation of the control system. If no function has been selected by the operator by means of a switch or button or otherwise, the system will operate in a pressure measurement mode and, in the absence of a flush inhibit command, will direct a flush of the catheter lines at specific intervals, e.g., for about 3 seconds every one minute. Once the flush cycle has been completed, the computer will automatically return to the pressure measurement mode and continue to interrogate the system for a selected function input. Thus, it can be said that the stopcocks are maintained by the computer in a pressure measurement condition as a default condition and will execute flushing at specified intervals and for specific durations throughout the default condition. The pressure measurement condition is shown in FIG. 2 and the flush condition is shown in FIG. 3.

One of the functions which can be selected is flushing of the pressure dome in order to purge the system of air bubbles. The hydraulic connection for this operation is shown in FIG. 5, and is usually performed at least before each procedure in order to eliminate air bubbles in the system. In one embodiment, stopcock 16 will not be connected to the automated system, but rather will be manipulated by hand in order to allow the operator to impart agitation of the pressure measurement device to jolt the bubbles free from their normally lodged condition. Once this operation has been completed, the operator can then return the system to a pressure measurement mode shown in FIG. 2.

When a pressure recording is to be taken, the operator will first calibrate the recording instruments by making a zero calibration with respect to the ambient atmosphere. The hydraulic communication path for this is shown in FIG. 4 and will be effected by merely actuating the appropriate control to the computer control means and zeroing the recording device while the pressure measuring means is exposed to the ambient pressure. Once this is completed, the system will be flushed with pressurized flushing fluid as shown in FIG. 3 and then connected for pressure measurement as shown in FIG. 2. Since it is not desired to have a periodic flushing during a pressure, recording operation, a flush inhibit command will be sent to the computer control means to eliminate the periodic flushing operation which usually occurs in the pressure measurement mode.

Referring now to FIGS. 9-14, the present invention will be described. The stopcocks 101 can be arranged in a manifold 100 which contains any number of individual stopcocks connected by channels 127. A typical number of stopcocks used to simultaneously control arterial and venous catheters is five. Thus, manifold 100 has five stopcocks 101 and seven ports 102, 103 which provide access to room air or other devices or fluid communication lines, as shown in FIGS. 9A and 9C. For example a common configuration includes stopcock #1 and #5 to room air, #2 to the arterial line, #4 to the venous line, #3 to the pressurized flush solution. The end ports 103 are shown permanently connected to pressure transducer domes 104. The channels 127 and ports 102, 103 are connected in varying combinations by channels 128 in the stopcocks which are illustrated in cross section in FIG. 9B. See also FIG. 1.

The illustrated embodiment uses a transducer or transducers 105 which are affixed to the actuator system 106 and which are coupled to the transducer dome or domes 104 of the disposable manifold 100. The fluid contents of the domes 104 are contiguous with the fluid system via the stopcock manifold system 100. The domes are flushed via conventional screw valves 126. There is a mechanical coupling means consisting of a membrane 107 incorporated in the structure of the transducer dome 104 and a second matching membrane 108 incorporated in the transducer 105 which are held in opposition by a suitable latching or locking means. The membrane 107 is viewed through a clear plastic dome structure in FIG. 9A and directly in FIG. 9C. The locking means is provided by a tapered edge 109 which, with rotation as shown by the arrows 110, engages a restraining means consisting of plastic tabs 111 which protrude from the circumferential inner walls of the transducer dome housing. This mechanical coupling transmits the pressure from the fluid contents of the dome 112 to the sensing means within the transducer. One commercially available embodiment of such a dome/transducer system is manufactured by Medex Inc., Columbus, Ohio. The fluid contents of the dome does not make physical contact with the transducer. The advantage of using such a compartmentalized system is that it eliminates the need for sterilizing the transducer between cases. The locking means which holds the dome against the transducer can simultaneously hold the rotational shafts 113 from the actuator in the mating receptacles 114 of the stopcocks.

It may be desirable to include pressure transducers in the system as a matter of convenience and possible cost savings. A disposable pressure transducer or transducers (not shown) can be attached to one or more ports of the manifold so that they are already in position when the manifold is engaged. Alternatively, the manifold could incorporate a transducer directly into its construction. This would eliminate the need for a port and probably decrease or eliminate the collection of air bubbles at the site of the pressure transducer.

A preferred configuration is for the stopcocks 101 to be in a manifold 100 facing the medical personnel so that they have access to the stopcocks for manual positioning of the manual operators or handles 98 (e.g., if the system malfunctions or if an unanticipated stopcock configuration is desired). In a preferred form, the shafts 113 from the actuator are configured at their distal ends with a shape (e.g., a half moon) 122 which inserts into a mating receptacle 114 of the stopcocks, such that there is only one possible angular relationship between the mating elements. This assures that the angular position of the stopcocks 101 are related to the angular position of their respective motors 115 and the sensing means 116 which transmits the angular position information back to the microprocessor system in a predictable fashion. The sensing means 116 consists of a pair of phototransistors 117 and pairs of reflective tape on the undersurface of the rotational elements 118. Each of the three stopcock positions is coded by the tape. Position #1 (0 degrees) uses a reflective tape and a non-reflective tape (binary 10) which face respectively phototransistors #1 and #2. Position #2 (90 degrees) is coded as non-reflective/ reflective (binary 01). Position #3 (180 degrees) is coded as reflective/non-reflective (binary 11). Other forms of angular position sensing systems may be used.

To make it easier to perform the mating, it may be desirable to slightly taper the distal end 119 of the inserting shaft 113. A means to hold the stopcocks or stopcock manifold in position is required. This may be accomplished with a simple latch or spring which holds the manifold 100 against the actuator system 106. Alternatively, this function can be performed by the mating connector between the pressure dome and pressure transducer as described above.

Referring to FIG. 14, there is shown the manifold 100 with a plurality of stopcocks 101 with manual operators or handles 98 on one side thereof and receptacles 114 on the other side thereof for mating with the distal ends 119 of shafts 113. When the ends 119 are mated with the receptacles 114, the actuator system 106 is operable to automatically operate the stopcocks 101 and the handles 98 are operable as described above and as shown in the drawings to manually position the stopcocks if the system malfunctions or if an unexpected stopcock configuration is desired.

Turning the stopcock requires relatively low speed and high torque. Also, it is desirable to use physically small motors. There are small motors which can provide adequate torque directly. However, it may be desirable to use a gearing system in which the motor rotates faster than the stopcock, thereby increasing the torque delivered to the stopcock. A motor or motors 115 are shown with small gears 120 engaging larger gears 121 affixed to rotational elements 118. This provides increased torque to the shafts with decreased rotational speed.

The prior embodiment of FIGS. 1-8 describes a system which uses a stepper motor for rotating the stopcock. The type of motor used could also be a conventional "non-stepper" motor if such a motor had desirable characteristics such as small size. The same principles of using feedback (e.g., optical feedback) to provide positional information to the microprocessor system would still be preferred.

With respect to the remote control of the system, one of the advantages of a microprocessor based control system is that it allows multiple individuals from multiple locations to control stopcock position. The control panel can be duplicated and wired in parallel with the main control panel. The remote control may be hard wired to the main control system. Alternatively, remote control can be provided by at least one wireless remote controller 123 (FIG. 12) such as those used to control a television set. The standard technology for such controllers is infrared transmission.

As described above, a feedback means 116 provides the microprocessor with information about the rotational position of each stopcock. In the described embodiment, the feedback is electrooptical. It could also be electromechanical or accomplished by some other means. By using this information the system can be designed to be "programmable". The user can set up a configuration of stopcocks to perform a particular function. The microprocessor "knows" the positions of the stopcocks through the feedback means. This information is stored and the configuration is assigned to a pushbutton 124 which will recall the particular combination of stopcock positions when it is pushed. Thus, in a somewhat similar fashion to saving favorite stations on a car radio, the system can be programmed to accommodate the particular desires of the physician using the system. The assignments given to the pushbuttons can be different for different physicians by simply storing and recalling multiple configurations as required. A different template 125 (which can be laid over the pushbutton controller indicating the function of each control button) is provided for each stored configuration. This provides a high degree of flexibility which can accommodate the different stopcock configurations used by different doctors.

It may also be desirable to modify the sequence of events as well as the stopcock configurations to accommodate the desires of different system users. It should be clear that this may be accomplished through modifications of the software. For example, the system can be configured to provide an audible warning tone which precedes an automatic flush. This could give the system user time to abort the flush if desired. Alternatively, the automatic flush could be replaced by a reminder tone which prompts the physician to perform the flush manually.

It would also be useful to have an air bubble detector incorporated into the system. Such devices are well described and commercially available. Such a detector could be positioned to sense the introduction of air into the flush solution, e.g., before it enters the manifold 100 and to provide a signal to the microprocessor which would prevent flushing of the system until the bubble condition is corrected.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. An automatic stopcock operating system for use in carrying out medical procedures comprising:
   a stopcock manifold for making fluid connections among a plurality of fluid sources associated with medical procedures, said manifold comprising a manifold body, a plurality of stopcocks mounted in said manifold body, each of said stopcocks having a handle on one side thereof for manually operating the stopcock associated therewith, each of said stopcocks having a connector on the other side thereof;
   means for communicating at least some of said stopcocks with one or more of said fluid sources;
   actuator means for automatically operating said stopcocks, said actuator means comprising a plurality of shafts, each shaft having a coupling for releasably and operatively coupling such shaft to a respective one of said stopcock connectors, said actuator means further comprising a motor operatively connected to said shaft for rotating said shaft to thereby automatically operate the stopcock associated therewith.

2. The stopcock manifold of claim 1, wherein said manifold body includes channels connecting said stopcocks in fluid communication, said means for communicating said stopcocks with said fluid sources comprising a plurality of first parts in said manifold adapted to connect each of said stopcocks with a respective fluid source.

3. The stopcock manifold of claim 2, including a plurality of second ports in said manifold adapted to be in fluid communication with the stopcocks and channels in the manifold body, a fluid pressure dome connected to at least one of said second ports.

4. The stopcock manifold of claim 3, wherein said actuator means comprises a pressure transducer for sensing pressure and means for coupling said pressure transducer to said pressure dome whereby the pressure transducer senses the pressure in said pressure dome.

5. The stopcock means of claim 3, including means for flushing said fluid pressure dome.

6. The stopcock means of claim 2, including a source of pressurized flush solution connected to one of said first ports for flushing the manifold.

7. The stopcock manifold of claim 1, including a microprocessor and means for sensing the rotational position of each of said shafts and for transmitting rotational position information to said microprocessor.

8. The stopcock manifold of claim 7, wherein said rotational position sensing means comprises an electro-optical or electromechanical sensor.

9. The stopcock means of claim 7, wherein said microprocessor includes programmable means for storing predetermined shaft rotational position information and control means for recalling the stored shaft rotational position information and transmitting it to the actuator means to position the shafts in a predetermined position.

10. The stopcock means of claim 9, including remote control means for remotely operating the microprocessor to control the rotational positions of the shafts.

11. The stopcock manifold of claim 1, including gear means operatively coupling said motors to said shafts for increasing the torque delivered to said shafts.

12. The stopcock operating system of claim 1, further comprising a microprocessor, means for sensing the rotational position of each of said shafts and for transmitting shaft rotational position information to said microprocessor, and wireless remote control means for remotely operating the microprocessor to automatically control the rotational positions of the shafts and thereby the operative positions of the stopcocks.

13. The stopcock operating system of claim 1, wherein said manifold body further comprises at least one pressure dome integrally connected thereto and in fluid communication with one of said fluid sources through one of said stopcocks, the pressure in said pressure dome corresponding to the pressure of said one fluid source, said actuator means further comprising at least one pressure transducer releasably coupled to said one pressure dome for sensing the pressure in said pressure dome.

14. The stopcock operating system of claim 13, wherein said manifold body includes a central fluid channel, each of said stopcocks having an operative position in which the stopcock is in fluid communication with said central fluid channel.

15. The stopcock operating system of claim 13, including means for releasably connecting the stopcock manifold to said actuator means.

16. The stopcock operating system of claim 1, wherein said connector for each stopcock comprises a receptacle, a respective one of said shafts being matingly and releasably engageable in the receptacle of a respective connector.

* * * * *